(12) United States Patent
McIntyre et al.

(10) Patent No.: US 7,862,552 B2
(45) Date of Patent: Jan. 4, 2011

(54) MEDICAL DEVICES FOR TREATING UROLOGICAL AND UTERINE CONDITIONS

(75) Inventors: Jon T. McIntyre, Newton, MA (US); Kenneth Daignault, Holden, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 355 days.

(21) Appl. No.: 11/125,296

(22) Filed: May 9, 2005

(65) Prior Publication Data
US 2006/0264912 A1 Nov. 23, 2006

(51) Int. Cl.
*A61K 9/22* (2006.01)
(52) U.S. Cl. .................. 604/891.1; 604/523; 604/8; 604/544
(58) Field of Classification Search .......... 604/8, 604/19, 21, 27, 36, 48, 502, 506, 523, 544, 604/73, 83, 93.01, 95.02, 164.01, 164.12, 604/171, 239, 264, 272, 277, 891.1
See application file for complete search history.

(56) References Cited

U.S. PATENT DOCUMENTS

| | | | | |
|---|---|---|---|---|
| 3,896,819 A | 7/1975 | Zaffaroni et al. | ............. | 128/130 |
| 3,933,152 A | 1/1976 | Moulding | ............. | 128/129 |
| 3,934,580 A | 1/1976 | Cournut | ............. | 128/130 |
| 3,935,860 A | 2/1976 | Hoff | ............. | 128/130 |
| 3,937,217 A | 2/1976 | Kosonen | ............. | 128/130 |
| 3,948,254 A | 4/1976 | Zaffaroni | ............. | 128/127 |
| 3,948,262 A | 4/1976 | Zaffaroni | ............. | 128/260 |
| 3,965,891 A | 6/1976 | Lerner | ............. | 128/130 |
| 3,967,618 A | 7/1976 | Zaffaroni | ............. | 128/130 |
| 3,993,057 A | 11/1976 | Ramwell | ............. | 128/130 |
| 3,993,058 A | 11/1976 | Hoff | ............. | 128/130 |
| 3,993,073 A | 11/1976 | Zaffaroni | ............. | 128/260 |
| 3,996,933 A | 12/1976 | Gutnick | ............. | 128/130 |
| 4,005,707 A | 2/1977 | Moulding, Jr. | ............. | 128/130 |
| 4,012,497 A | 3/1977 | Schopflin | ............. | 424/22 |
| 4,014,988 A | 3/1977 | Pharriss et al. | ............. | 424/14 |
| 4,016,270 A | 4/1977 | Pharriss et al. | ............. | 424/242 |
| 4,018,220 A | 4/1977 | Emmett | ............. | 128/130 |
| RE29,231 E | 5/1977 | Leeds | ............. | 260/885 |

(Continued)

FOREIGN PATENT DOCUMENTS

EP    0024780 B1    10/1984

(Continued)

OTHER PUBLICATIONS

C. Lowell Parsons, "Evidence-based strategies for recognizing and managing IC," *Contemporary Urology*, vol. 15, No. 2, Feb. 2003, pp. 22-35.

(Continued)

*Primary Examiner*—Nicholas D Lucchesi
*Assistant Examiner*—Quynh-Nhu H Vu
(74) *Attorney, Agent, or Firm*—Mayer & Williams PC; David B. Bonham; Keum J. Park (57) ABSTRACT

The present invention relates to implantable or insertable medical devices that treat uterine and urological conditions that cause chronic pelvic pain and other symptoms. In another aspect, the present invention relates to methods of manufacturing such implantable or insertable medical devices.

26 Claims, 4 Drawing Sheets

U.S. PATENT DOCUMENTS

| | | | |
|---|---|---|---|
| 4,022,198 A | 5/1977 | Johnson | 128/130 |
| 4,023,678 A | 5/1977 | Fiedler | 206/363 |
| 4,026,281 A | 5/1977 | Mayberry et al. | 128/130 |
| 4,034,749 A | 7/1977 | Von Kesserü et al. | 128/130 |
| 4,038,978 A | 8/1977 | Morris et al. | 128/127 |
| 4,040,417 A | 8/1977 | Zipper | 128/130 |
| 4,054,131 A | 10/1977 | Kessel | 128/130 |
| 4,094,313 A | 6/1978 | Komamura et al. | 128/130 |
| 4,111,196 A | 9/1978 | Emmett | 128/130 |
| 4,111,302 A | 9/1978 | Roth | 206/363 |
| 4,117,838 A | 10/1978 | Hasson | 128/130 |
| 4,117,839 A | 10/1978 | Morris | 128/130 |
| 4,143,656 A | 3/1979 | Holmes | 128/130 |
| 4,146,023 A | 3/1979 | Pope | 128/130 |
| 4,156,067 A | 5/1979 | Gould | 528/73 |
| 4,180,064 A | 12/1979 | Heller et al. | 128/130 |
| 4,198,966 A | 4/1980 | Kaivola | 128/130 |
| 4,200,091 A | 4/1980 | Del Conte | 128/130 |
| RE30,312 E | 6/1980 | Kessel | 128/130 |
| 4,233,968 A | 11/1980 | Shaw, Jr. | 128/130 |
| 4,249,525 A | 2/1981 | Krzeminski | 128/130 |
| 4,283,325 A | 8/1981 | Berthet et al. | 260/37 |
| 4,284,074 A | 8/1981 | Shaw, Jr. | 128/130 |
| 4,326,511 A | 4/1982 | Zimerman | 128/130 |
| 4,341,728 A | 7/1982 | Robertson et al. | 264/161 |
| 4,344,431 A | 8/1982 | Yolles | 128/260 |
| 4,351,326 A | 9/1982 | Kosonen | 128/130 |
| 4,359,046 A | 11/1982 | Shaw, Jr. | 128/130 |
| 4,372,302 A | 2/1983 | Åkerlund | 128/130 |
| 4,381,001 A | 4/1983 | Shaw, Jr. | 128/130 |
| 4,424,305 A | 1/1984 | Gould et al. | 525/127 |
| 4,428,371 A | 1/1984 | Krzeminski | 128/130 |
| 4,476,871 A | 10/1984 | Hon | 128/642 |
| 4,495,934 A | 1/1985 | Shaw, Jr. | 128/130 |
| 4,496,535 A | 1/1985 | Gould et al. | 424/19 |
| 4,531,933 A * | 7/1985 | Norton et al. | 604/8 |
| 4,542,169 A | 9/1985 | Costerton | 424/83 |
| 4,549,652 A | 10/1985 | Free | 206/363 |
| 4,552,557 A | 11/1985 | Rangaswamy | 604/96 |
| 4,553,536 A | 11/1985 | Chiozza | 128/130 |
| 4,561,433 A | 12/1985 | Wheeler et al. | 128/130 |
| 4,562,835 A | 1/1986 | Anderson | 128/130 |
| 4,572,162 A | 2/1986 | Livesay et al. | 128/1 R |
| 4,578,076 A | 3/1986 | Luukkainen et al. | 604/892 |
| 4,582,052 A | 4/1986 | Dunn et al. | 128/130 |
| 4,612,924 A | 9/1986 | Cimber | 128/130 |
| 4,628,924 A | 12/1986 | Cimber | 128/130 |
| 4,655,204 A | 4/1987 | Basuyaux | 128/130 |
| 4,658,810 A | 4/1987 | Bauer | 128/130 |
| 4,665,906 A | 5/1987 | Jervis | 128/92 YN |
| 4,708,134 A | 11/1987 | Wildemeersch | 128/130 |
| 4,715,365 A | 12/1987 | Cimber | 128/130 |
| 4,721,105 A | 1/1988 | Wildemeersch | 128/130 |
| 4,740,195 A * | 4/1988 | Lanciano | 604/533 |
| 4,789,720 A | 12/1988 | Teffenhart | 528/76 |
| 4,807,610 A | 2/1989 | Gainutdinova et al. | 128/830 |
| 4,810,582 A | 3/1989 | Gould et al. | 428/423 |
| 4,813,925 A * | 3/1989 | Anderson et al. | 604/8 |
| 4,830,025 A | 5/1989 | Gainutdinova et al. | 128/839 |
| 4,841,991 A | 6/1989 | Gainutdinova et al. | 128/833 |
| 4,849,406 A | 7/1989 | Salonen | 514/8 |
| 4,927,806 A | 5/1990 | Kramer et al. | 514/2 |
| 4,940,051 A | 7/1990 | Lankinen | 128/200.18 |
| 5,008,388 A | 4/1991 | Ingberg et al. | 540/145 |
| 5,067,957 A | 11/1991 | Jervis | 606/108 |
| 5,145,859 A | 9/1992 | Fleischmann | 514/356 |
| 5,175,376 A | 12/1992 | Nieminen et al. | 568/781 |
| 5,190,546 A | 3/1993 | Jervis | 606/78 |
| 5,213,266 A | 5/1993 | Lankinen | 239/338 |
| 5,230,207 A | 7/1993 | Hartzell et al. | 53/547 |
| 5,237,094 A | 8/1993 | Lampi et al. | 562/22 |
| 5,237,095 A | 8/1993 | Godfrey, Jr. et al. | 562/506 |
| 5,261,211 A | 11/1993 | Hartzell et al. | 53/452 |
| 5,295,479 A | 3/1994 | Lankinen | 128/203.15 |
| 5,321,113 A | 6/1994 | Cooper et al. | 528/176 |
| 5,347,794 A | 9/1994 | Hartzell et al. | 53/547 |
| 5,348,062 A | 9/1994 | Hartzell et al. | 141/186 |
| 5,369,943 A | 12/1994 | Helle et al. | 53/567 |
| 5,376,649 A | 12/1994 | Pohjala et al. | 514/108 |
| 5,393,748 A | 2/1995 | Pohjala et al. | 514/89 |
| 5,400,804 A | 3/1995 | Helle et al. | 128/898 |
| 5,403,829 A | 4/1995 | Lehtinen et al. | 514/102 |
| 5,409,816 A | 4/1995 | Lundell et al. | 435/713 |
| 5,433,217 A | 7/1995 | Pianetti | 128/830 |
| 5,438,048 A | 8/1995 | Nikander et al. | 514/108 |
| 5,442,101 A | 8/1995 | Hanhijävi et al. | 562/10 |
| 5,476,079 A | 12/1995 | Kanamori et al. | 123/458 |
| 5,476,093 A | 12/1995 | Lankinen | 128/203.15 |
| 5,478,339 A | 12/1995 | Tadir et al. | 606/15 |
| 5,494,047 A | 2/1996 | Van Os | 12/832 |
| 5,525,354 A | 6/1996 | Posti et al. | 424/451 |
| 5,541,184 A | 7/1996 | Perälampi | 514/236.2 |
| 5,554,147 A | 9/1996 | Batich et al. | 604/890.1 |
| 5,555,896 A | 9/1996 | Cimber | 128/830 |
| 5,558,637 A | 9/1996 | Allonen et al. | 604/60 |
| 5,574,151 A | 11/1996 | Toikka | 536/124 |
| 5,595,751 A | 1/1997 | Bezwada et al. | 424/422 |
| 5,597,378 A | 1/1997 | Jervis | 606/78 |
| 5,597,579 A | 1/1997 | Bezwada et al. | 424/426 |
| 5,607,417 A | 3/1997 | Batich et al. | 604/890.1 |
| 5,607,687 A | 3/1997 | Bezwada et al. | 424/426 |
| 5,618,552 A | 4/1997 | Bezwada et al. | 424/426 |
| 5,620,697 A | 4/1997 | Törmälä et al. | 424/426 |
| 5,620,698 A | 4/1997 | Bezwada et al. | 424/426 |
| 5,626,148 A | 5/1997 | Lehtinen | 128/830 |
| RE35,552 E | 7/1997 | Lankinen | 128/203.12 |
| 5,645,850 A | 7/1997 | Bezwada et al. | 424/426 |
| 5,681,817 A | 10/1997 | Hodgen et al. | 514/12 |
| 5,694,947 A | 12/1997 | Lehtinen | 128/833 |
| 5,698,213 A | 12/1997 | Jamiolkowski et al. | 424/426 |
| 5,719,196 A | 2/1998 | Uhari et al. | 514/738 |
| 5,733,564 A | 3/1998 | Lehtinen | 424/423 |
| 5,776,499 A | 7/1998 | Pohjala et al. | 424/489 |
| 5,785,053 A | 7/1998 | Macandrew et al. | 128/840 |
| 5,827,984 A | 10/1998 | Sinnreich et al. | 73/866 |
| 5,854,383 A | 12/1998 | Erneta et al. | 528/354 |
| 5,866,556 A | 2/1999 | Heikkilä-Hoikka et al. | 514/89 |
| 5,876,434 A | 3/1999 | Flomenbliit et al. | 623/1 |
| 5,919,755 A | 7/1999 | Kangasaho et al. | 514/6 |
| 5,951,997 A | 9/1999 | Bezwada et al. | 424/426 |
| 5,981,470 A | 11/1999 | Ahmed | 514/2 |
| 6,004,260 A | 12/1999 | Thompson | 600/33 |
| 6,004,580 A | 12/1999 | Backlund et al. | 424/450 |
| 6,056,976 A | 5/2000 | Markkula et al. | 424/486 |
| 6,063,395 A | 5/2000 | Markkula et al. | 424/422 |
| 6,066,677 A | 5/2000 | Uhari et al. | 514/738 |
| 6,074,660 A | 6/2000 | Jamiolkowski et al. | 424/426 |
| 6,083,916 A | 7/2000 | Nonomura et al. | 514/15 |
| 6,083,938 A | 7/2000 | Heikkilä-Hoikka et al. | 514/89 |
| 6,117,442 A | 9/2000 | Markkula et al. | 424/422 |
| 6,119,696 A | 9/2000 | Turin | 128/830 |
| 6,132,394 A | 10/2000 | Lankinen | 604/58 |
| 6,156,049 A | 12/2000 | Lovato et al. | 606/170 |
| 6,168,777 B1 | 1/2001 | Greff et al. | 424/1.25 |
| 6,207,696 B1 | 3/2001 | Peterson et al. | 514/400 |
| 6,224,894 B1 | 5/2001 | Jamiolkowski et al. | 424/426 |
| 6,231,591 B1 | 5/2001 | Desai | 606/210 |
| 6,277,391 B1 | 8/2001 | Seo et al. | 424/426 |
| 6,293,923 B1 | 9/2001 | Yachia et al. | 604/96.01 |
| 6,299,894 B1 | 10/2001 | Markkula et al. | 424/422 |
| 6,300,452 B1 | 10/2001 | Jukarainen et al. | 528/15 |
| 6,306,422 B1 | 10/2001 | Batich et al. | 424/423 |
| 6,326,363 B1 | 12/2001 | Pohjala et al. | 514/103 |
| 6,329,428 B1 | 12/2001 | Yamauchi et al. | 514/538 |

| | | | | |
|---|---|---|---|---|
| 6,461,296 B1 | 10/2002 | Desai .................. 600/210 | EP 0577913 B1 | 6/1997 |
| 6,476,079 B1 | 11/2002 | Jukarainen et al. ....... 514/772.4 | EP 0798999 A1 | 10/1997 |
| 6,491,672 B2 | 12/2002 | Slepian et al. ............ 604/267 | EP 0799066 A1 | 10/1997 |
| 6,494,844 B1 | 12/2002 | Van Bladel et al. ......... 600/567 | EP 0806951 A1 | 11/1997 |
| 6,495,164 B1 | 12/2002 | Ramstack et al. ............ 424/489 | EP 0676956 B1 | 3/1998 |
| 6,537,566 B1 | 3/2003 | Copland et al. ............. 424/422 | EP 0570380 B1 | 9/1998 |
| 6,544,227 B2 | 4/2003 | Sahatjian et al. ............ 604/113 | EP 0703802 B1 | 3/1999 |
| 6,565,530 B2 | 5/2003 | Sahatjian et al. ............ 604/113 | EP 0723465 B1 | 2/2000 |
| 6,582,389 B2 | 6/2003 | Buzot .................... 604/15 | EP 0563096 B1 | 5/2000 |
| 6,642,274 B1 | 11/2003 | Neal ...................... 514/573 | EP 0563107 B1 | 5/2000 |
| 6,648,863 B2 | 11/2003 | Reever .................... 604/327 | EP 1005501 A1 | 6/2000 |
| 6,656,146 B1 | 12/2003 | Clayman et al. ............. 604/8 | EP 0673629 B1 | 7/2000 |
| 6,685,745 B2 | 2/2004 | Reever .................... 623/23.7 | EP 0696923 B1 | 7/2000 |
| 6,719,804 B2 * | 4/2004 | St. Pierre ................ 623/23.7 | EP 0477222 B1 | 8/2000 |
| 2001/0047147 A1 | 11/2001 | Slepian et al. .............. 604/22 | EP 1027037 A1 | 8/2000 |
| 2002/0010150 A1 | 1/2002 | Cortese et al. .............. 514/54 | EP 1032578 A1 | 9/2000 |
| 2002/0068089 A1 | 6/2002 | Vogel et al. ................ 424/490 | EP 1041971 A1 | 10/2000 |
| 2002/0082610 A1 | 6/2002 | Cioanta et al. .............. 606/108 | EP 1 078 636 A1 | 2/2001 |
| 2002/0115992 A1 | 8/2002 | Utley et al. ................ 606/41 | EP 0689443 B1 | 5/2001 |
| 2002/0176893 A1 | 11/2002 | Wironen et al. ............. 424/489 | EP 0727983 B1 | 7/2001 |
| 2003/0050638 A1 | 3/2003 | Yachia et al. ............... 606/45 | EP 0760651 B1 | 7/2001 |
| 2003/0064998 A1 | 4/2003 | Francois et al. ........ 514/259.41 | EP 1128810 A1 | 9/2001 |
| 2003/0093157 A1 | 5/2003 | Casares et al. ............ 623/23.73 | EP 1128811 A1 | 9/2001 |
| 2003/0100830 A1 | 5/2003 | Zhong et al. ............... 600/431 | EP 0762883 B1 | 11/2001 |
| 2003/0153983 A1 | 8/2003 | Miller et al. ............... 623/23.7 | EP 1151030 A1 | 11/2001 |
| 2003/0171678 A1 | 9/2003 | Batten et al. ............... 600/443 | EP 0799066 B1 | 1/2002 |
| 2004/0037887 A1 | 2/2004 | Bourne et al. .............. 424/486 | EP 1 197 208 A1 | 4/2002 |
| 2004/0096514 A1 | 5/2004 | Vogel et al. ................ 424/489 | EP 1239829 A1 | 9/2002 |
| 2005/0064008 A1 | 3/2005 | Bucay-Couto et al. ...... 424/423 | EP 1265664 A1 | 12/2002 |
| 2005/0064045 A1 | 3/2005 | Zhong et al. ................ 424/680 | EP 0798999 B1 | 3/2003 |

FOREIGN PATENT DOCUMENTS

| | | | | |
|---|---|---|---|---|
| EP | 0372137 | 6/1990 | GB 811.717 | 4/1959 |
| EP | 0511947 A1 | 11/1992 | GB 1414812 | 11/1975 |
| EP | 0570380 A1 | 11/1993 | WO WO 9216629 A1 | 10/1992 |
| EP | 0577591 A1 | 1/1994 | WO WO 9300055 A1 | 1/1993 |
| EP | 0577592 A1 | 1/1994 | WO WO 9307162 A1 | 4/1993 |
| EP | 0577593 A1 | 1/1994 | WO WO 9324466 A1 | 12/1993 |
| EP | 0577913 A1 | 1/1994 | WO WO 9401115 A1 | 1/1994 |
| EP | 0589938 A1 | 4/1994 | WO WO 9403143 A1 | 2/1994 |
| EP | 0440684 B1 | 9/1994 | WO WO 9403144 A1 | 2/1994 |
| EP | 0490907 B1 | 12/1994 | WO WO 9404134 A1 | 3/1994 |
| EP | 0470086 B1 | 1/1995 | WO WO 9416091 A1 | 7/1994 |
| EP | 0637236 A1 | 2/1995 | WO WO 9421266 A1 | 9/1994 |
| EP | 0640343 A1 | 3/1995 | WO WO 9423770 A1 | 10/1994 |
| EP | 0642501 A1 | 3/1995 | WO WO 9500118 A1 | 1/1995 |
| EP | 0652737 A1 | 5/1995 | WO WO 9500143 A1 | 1/1995 |
| EP | 0652738 A1 | 5/1995 | WO WO 9500144 A1 | 1/1995 |
| EP | 0655911 A1 | 6/1995 | WO WO 9500199 A1 | 1/1995 |
| EP | 0479813 B1 | 9/1995 | WO WO 9501161 A1 | 1/1995 |
| EP | 0677116 A1 | 10/1995 | WO WO 9510314 A1 | 4/1995 |
| EP | 0798999 B1 | 12/1995 | WO WO 9513054 A1 | 5/1995 |
| EP | 0689443 A1 | 1/1996 | WO WO 9513078 A1 | 5/1995 |
| EP | 0696923 A1 | 2/1996 | WO WO 9526711 A1 | 10/1995 |
| EP | 0703777 A1 | 4/1996 | WO WO 9526712 A1 | 10/1995 |
| EP | 0703802 A1 | 4/1996 | WO WO 9531969 A1 | 11/1995 |
| EP | 0708636 A1 | 5/1996 | WO WO 9532752 A1 | 12/1995 |
| EP | 0577593 B1 | 6/1996 | WO WO 9533466 A1 | 12/1995 |
| EP | 0511947 B1 | 7/1996 | WO WO 9601092 A1 | 1/1996 |
| EP | 0577592 B1 | 7/1996 | WO WO 9612477 A1 | 5/1996 |
| EP | 0723465 A1 | 7/1996 | WO WO 9618365 A1 | 6/1996 |
| EP | 0727983 A1 | 8/1996 | WO WO 9623495 A1 | 8/1996 |
| EP | 0533683 B1 | 9/1996 | WO WO 9627607 A1 | 9/1996 |
| EP | 0637236 B1 | 10/1996 | WO WO 9803165 A1 | 1/1998 |
| EP | 0577591 B1 | 1/1997 | WO WO 9910412 A1 | 3/1999 |
| EP | 0752847 A1 | 1/1997 | WO WO 9915155 A1 | 4/1999 |
| EP | 0755246 A1 | 1/1997 | WO WO 9920634 A1 | 4/1999 |
| EP | 0760651 A1 | 3/1997 | WO WO 9933471 A1 | 7/1999 |
| EP | 0762883 A1 | 3/1997 | WO WO 9934778 A1 | 7/1999 |
| EP | 0652737 B1 | 4/1997 | WO WO 0000550 A1 | 1/2000 |
| EP | 0652738 B1 | 4/1997 | WO WO 0028967 A1 | 5/2000 |
| EP | 0768850 A1 | 4/1997 | WO WO 0028968 A1 | 5/2000 |
| | | | WO WO 0029464 A1 | 5/2000 |
| | | | WO WO 00/64513 | 11/2000 |
| | | | WO WO 0147490 A1 | 7/2001 |

| | | |
|---|---|---|
| WO | WO 0168168 A1 | 9/2001 |
| WO | WO 0185132 A1 | 11/2001 |
| WO | WO 0185133 A1 | 11/2001 |
| WO | WO 0232433 A1 | 4/2002 |
| WO | WO 0234269 A1 | 5/2002 |
| WO | WO 03/005889 A2 | 1/2003 |
| WO | WO 03011905 A1 | 2/2003 |
| WO | WO 03017971 A1 | 3/2003 |
| WO | WO 2004/010975 A2 | 2/2004 |

OTHER PUBLICATIONS

C. Lowell Parsons et al., "Gynecologic Presentation of Interstitial Cystitis as Detected by Intravesical Potassium Sensitivity," *Obstetrics & Gynecology*, vol. 98, No. 1, Jul. 2001, pp. 127-132.

C. Lowell Parsons et al., "The prevalence of interstitial cystitis in gynecologic patients with pelvic pain, as detected by intravesical potassium sensitivity," *American Journal of Obstetrics and Gynecology*, vol. 187, No. 5, Nov. 2002, pp. 1395-1400.

Levie, Mark D., MD, Highlights from the American Association of Gynecologic Laparoscopists 32$^{nd}$ Annual Meeting, Medscape Ob/GYN & Women's Health 8(2), Nov. 18-22, 2003, Las Vegas, NV.

Peterson, Lynne, Summary of American Urogynecologic Society meeting, Sep. 11-13, 2003, Hollywood, FL, Trends-in-Medicine, Sep. 2003, 6 pp.

Dmochowski, Roger R., "Advances in the Treatment of Stress Urinary Incontinence: Bulking Therapy," *Reviews in Urology*, vol. 7, Suppl. 1, 2005, pp. S1-S2.

Kerr, Lindsey A., "Bulking Agents in the Treatment of Stress Urinary Incontinence: History, Outcomes, Patient Populations, and Reimbursement Profile," *Reviews in Urology*, vol. 7, Suppl. 1, 2005, pp. S3-S11.

Herschorn, Sender, "Current Use of Injectable Agents for Female Stress Urinary Incontinence," *Reviews in Urology*, vol. 7, Suppl. 1, 2005, pp. S12-S21.

Parsons, C. Lowell, "Evidence-Based Strategies for Recognizing and Managing IC," Contemporary Urology, vol. 15, No. 2, Feb. 2003, pp. 22-35.

WHC-Copper T IUD Information. http://wyhc.org/knowyouroptions/BCO/IUD-CopperT.asp. 6/20/2003 download, 2 pp.

WHC-Levonorgestrel IUD Information. http://wyhc.org/knowyouroptions/BCO/IUD-levonorgestrel.asp. 6/20/2003 download, 1 p.

WHC-Progestasert IUD Information. http://wyhc.org/knowyouroptions/BCO/IUD-Progestasert.asp. 6/20/2003 download, 1 p.

Mirena information. http://www.mirena-us.com. Jun. 26, 2003 download, 9 pp.

* cited by examiner

MEDICAL DEVICES FOR TREATING UROLOGICAL AND UTERINE CONDITIONS

CROSS REFERENCE TO RELATED APPLICATIONS

This application is related to U.S. patent application Ser. No. 11/125,297, filed on May 9, 2005, and entitled "Injectable Bulking Compositions," which is incorporated by reference in its entirety herein.

This application is related to U.S. patent application Ser. No. 11/124,827, filed on May 9, 2005, and entitled "Method and Device For Tissue Removal And For Delivery Of A Therapeutic Agent Or Bulking Agent," which is incorporated by reference in its entirety herein.

This application is related to U.S. patent application Ser. No. 11/124,828, filed on May 9, 2005, and entitled "Method For Treatment of Uterine Fibroid Tumors," which is incorporated by reference in its entirety herein.

FIELD OF THE INVENTION

The present invention relates generally to medical devices which contain polymer regions for release of therapeutic agents. In particular, the present invention relates to implantable or insertable medical devices that treat pelvic pain caused by gynecological and urological conditions such as uterine fibroids, endometriosis, interstitial cystitis, and urethral syndrome, as well as methods for manufacturing such devices.

BACKGROUND OF THE INVENTION

Interstitial cystitis ("IC") is a chronic progressive disorder of the lower urinary tract affecting both men and women marked by an inflammation or irritation of the bladder leading to urinary urgency, frequency and/or tenderness or pain in the bladder and surrounding pelvic area. Recent studies have indicated that up to 80-85% of women of the approximately nine million women who suffer from chronic pelvic pain may have interstitial cystitis (see Parsons et al., "Gynecologic presentation of interstitial cystitis as detected by intravesical potassium sensitivity," *Obstet Gynecol*, 98(1):127-132 (2001); Parsons et al., "The prevalence of interstitial cystitis in gynecologic patient with pelvic pain as detected by intravesical potassium sensitivity," *Am J Obstet Gynecol*, 187(5): 1395-1400 (2002), the contents of both of which are incorporated by reference in their entirety).

Though its etiology is unknown, it is believed that the protective layer of glycosaminoglycans (GAG) that protects the inner epithelial lining of the bladder is somehow disrupted, allowing substances in the urine to irritate the underlying epithelial cells. This disruption in the GAG lining is believed to be caused by an unidentified infection, perhaps of viral origin, that is disrupting the GAG lining or damaging the bladder wall directly, by a substance in the urine that causes the damage, and/or by an autoimmune response following a bladder infection.

Urethral syndrome is a related painful voiding disorder of unknown etiology affecting women exhibiting many similar symptoms set forth above.

Unlike some other diseases of the genitourinary system, such as common cystitis, urethritis, and nephritis, and bacterial prostatitis, IC and urethral syndrome generally do not respond to antibiotic therapy. For most IC patients, and for patients with prostatodynia, a related condition that occurs in men, therapy includes heparinoid therapy with oral pentosan polysulfate (PPS; Elmiron©, Ortho-McNeil/Alza), typically 300-600 mg daily, intravesical heparin (40,000 units in 8 ml of 1% lidocaine and 3 ml sodium bicarbonate once or twice daily), or both. This therapy is usually combined with oral pain medication, antidepressants (to reverse neural activation of bladder nerves that may cause symptoms of pain and urgency to persist even after the epithelium has been restored), and/or antihistamines (to control immune system mast cell degranulation that is believed to provoke IC symptom flares). Heparinoids are similar in structure to the glycosaminoglycans in the bladder surface mucus and are believed to help repair or restore the epithelium in individuals who have abnormal epithelial permeability.

Other therapy options includes bladder instillation wherein the bladder is temporarily filled with a solution containing a therapeutic agent such as dimethyl sulfoxide (DMSO), transcutaneous electrical nerve stimulation (TENS), which delivers mild electric pulses to the bladder area, and as a last resort, bladder surgery.

Despite these treatment options, there is a continuing need for alternative therapies that provide relief from IC symptoms, urethral syndrome and other urological symptoms and/or treat the underlying conditions that trigger these symptoms or prevent them from occurring.

Other leading causes of chronic pelvic pain are uterine fibroids and endometriosis. These two medical conditions affect millions of women in the U.S. and cost billions of dollars in health care dollars each year. Uterine fibroid tumors (also referred to as "uterine fibroids" or "leiomyomas") are non-cancerous smooth muscle tumors of the uterus. They are believed to occur in 20 percent to 50 percent of women, depending on age and race. Depending on their size and location, fibroids can cause a variety of symptoms, the most common of which are bleeding and "bulk" pelvic pain, and infertility. Some of the most common treatments for fibroids are quite invasive. For example, although a hysterectomy results in the complete removal of the uterus, approximately one-third of the hysterectomies in the United States each year are performed to treat uterine fibroids. Myomectomy is also commonly used to surgically remove uterine fibroids. However, about three-quarters of the myomectomy surgeries are open surgeries involving an abdominal incision. A more recently developed treatment is uterine artery embolization. During this procedure, a catheter is inserted into a femoral artery and guided to a uterine fibroid artery. Small particles are then injected from the catheter into the fibroid artery, blocking its blood supply and causing it to eventually shrink and die. Although this procedure is less invasive than the above procedures, it commonly results in pain-related post-surgical symptoms. Myolysis and cryomyolysis are other techniques in which uterine fibroids are burned or frozen via laproscopic surgery. Like uterine artery embolization, myolysis/cryomyolysis causes fibroids to die and shrink over time.

Endometriosis, although a separate disease, is believed to be often triggered by the same mechanisms that cause fibroids and can also significantly impact a woman's quality of life. Endometriosis is a condition where the endometrium (the lining of the uterus) is found in locations outside the uterus. This misplaced tissue may be found, for example, on the ovaries, outer wall of the uterus, bowel, bladder, utero-sacral ligaments (ligaments that hold the uterus in place) or peritoneum. On rare occasions, they may be found in distant sites such as the lungs or an armpit. As with fibroids, typical treatments include surgery to remove endometrial plaques by mechanical, electrical or laser means, and hysterectomy.

Non-surgical treatment options for both fibroids and endometriosis include oral administration of pain medication and hormonal therapy. For example, in the case of endometriosis, drug therapy includes non-steroidal anti-inflammatory drugs (NSAIDS) and hormonal therapy to interrupt ovarian function and control menstrual bleeding with hormones such as oral contraceptives, progestins, danazol, GnRH agonists, Mifepristone, selective progesterone receptor modulators (SPRMs) or aromatase inhibitors. Similarly, drug therapy for fibroids includes NSAIDS, oral contraceptives, and GnRH agonists.

For a significant fraction of patients, however, drug therapy, on its own, provides insufficient relief from symptoms caused by the fibroids and/or endometriosis and necessitates subsequent treatment with one of the surgical options discussed above. In addition, since the drugs are administered orally (i.e., systemically) and not directly to the fibroids or the endometrial cysts, the doses of drugs, particularly of hormonal drugs, required to disrupt ovarian function, menstrual bleeding, and/or cause fibroid shrinkage are high enough to cause undesirable side effects.

Hence, there is a continuing need for alternative therapies for the treatment of uterine fibroids and endometriosis, which are less invasive, which provide better relief from pelvic pain and discomfort, which preserve the patient's uterus, and which cause fewer side effects.

SUMMARY OF THE INVENTION

In an effort to alleviate the foregoing and other disadvantages of the prior art, Applicants have developed implantable or insertable medical devices suitable for short-term to long-term placement and/or implantation and a method for manufacturing such devices, wherein the devices provide in situ treatment of various uterine or urological conditions by delivering therapeutic agent(s) particularly suited for treating these conditions.

DETAILED DESCRIPTION OF THE PREFERRED EMBODIMENTS

The present invention is directed to urological and uterine devices for treating one or more of the diseases and/or conditions set forth above. As used herein, "treatment" refers to the prevention of a disease or condition, the reduction or elimination of symptoms associated with a disease or condition, or the substantial or complete elimination of a disease or condition. Preferred subjects (also referred to as "patients") are mammalian subjects, and more preferably are human subjects.

As noted above, the implantable or insertable medical devices of the present invention are suitable for short-term to long-term placement and/or implantation, meaning times ranging from 24 hours to 2 days to 4 days to 1 week to 2 weeks to 1 month to 3 months to 6 months to 12 months or even longer.

According to one aspect of the present invention, a urological medical device is provided comprising a first therapeutic agent for treating a urological condition, wherein the medical device is adapted, upon implantation or insertion into a patient, to release all or a majority of a first therapeutic agent from a portion of the medical device that occupies the urinary bladder. The urological condition may comprise any condition affecting the urinary tract such as common cystitis, urethritis, and nephritis, and bacterial prostatitis, IC and urethral syndrome, but particularly to those that affect the bladder, such as interstitial cystitis.

According to one embodiment of this aspect of the invention, a urological medical device is provided which resides partially in the urinary bladder and which extends upstream from the bladder, downstream from the bladder, or both. For example, the device can be a urethral stent which includes a tubular member having a bladder retention feature at the distal end of the tubular member, or a ureteral stent, which includes a tubular member, a renal retention feature at the distal end of the tubular member and a bladder retention feature at the proximal end of the tubular member. The portion of such a medical device that resides in the bladder (the "bladder portion") contains at least one release region that in turn controls the release of at least one therapeutic agent (which is disposed beneath or within the release region) for treating a urological condition. Moreover, in some embodiments, the therapeutic agent is either present exclusively in the bladder portion of the device, or is released from the bladder portion in concentrations that are greater (e.g., 1.5 times or more, 2 times or more, 3 times or more, 4 times or more, 5 times or more, 10 times or more, 25 times or more, 50 times or more, 100 times or more greater) than the concentrations released from other portions of the device. This can be achieved, for example, by providing concentrations of therapeutic agent in the bladder portion that are greater (e.g., by the above amounts) than the concentrations found in other portions of the device.

According to yet another embodiment of this aspect of the present invention, a urological medical device is provided where the therapeutic agent is released only from the portion of the medical device that occupies the urinary bladder. In other embodiments, the device resides completely in the urinary bladder.

The release regions of the above urological devices contain one or more polymers that may be selected from any biocompatible polymers that are suitable for use in implantable or insertable urological medical devices and are suitable for therapeutic agent release. (As used herein, the term "biocompatible" describes a material that is substantially not toxic to the human body, and that does not significantly induce inflammation or other adverse response in body tissues.)

The polymers may be substantially non-biodegradable or biodegradable. In other embodiments, the device comprises a second therapeutic agent, or a plurality of therapeutic agents. Typically, the therapeutic agent is disposed beneath or within at least one release region that comprises a biocompatible polymer. The release region can comprise one, two, or a plurality of biocompatible polymers.

An advantage of the urological devices of the present invention is that since the therapeutic agents are released from the devices in situ, e.g., near or inside the bladder, treatment is more direct, and less medication may be required as compared with typical systemic treatments such as oral pentosan polysulfate, antidepressant or antihistamine therapy.

Another advantage of certain urological devices of the present invention is that they may be selected for use in patients already requiring a stent or other device for another urological condition, such as a ureteral blockage or obstruction. The therapeutic agent(s) that are released from the device may treat the other condition (e.g., that caused by the blockage or obstruction) and/or treat other conditions such as interstitial cystitis.

According to another aspect of the present invention, a uterine device is provided, which is adapted to conform to the general contours of an interior cavity of a mammalian female uterus. According to one embodiment of this aspect, the invention comprises a uterine device for the treatment of a uterine condition comprising a contoured structure of a flexible material having the general contours of an interior cavity of a human female uterus wherein the device comprises a therapeutic agent for treating a uterine condition. The device comprises at least one release region that controls the release of at least one therapeutic agent (which is disposed beneath or within the release region) for treating a uterine condition.

At least one release region also contains at least one polymer that may be selected from any biocompatible polymers that are suitable for use in implantable or insertable uterine medical devices and are suitable for therapeutic agent release. The polymers may be substantially non-biodegradable or biodegradable and a device may comprise a plurality of biocompatible polymers.

An advantage of the uterine devices of the present invention is that since the therapeutic agent is released from the devices in situ, treatment is more direct, and less medication may be required as compared with typical systemic treatments such as oral contraceptives that may cause undesirable side effects. In particular, given that the devices are shaped to generally conform to the contours of the uterine cavity (e.g., the device comes into contact with the walls of the uterine cavity), an appreciable percentage of a surface of the device comes into contact with the uterine wall, facilitating direct and targeted release of the therapeutic agent into the uterine site.

Another advantage of the uterine devices of the present invention is that therapy using such devices is less invasive than surgical treatment options such as hysterectomy and myolysis.

Another advantage of the uterine device of the present invention is that since the device may be easily removed and replaced, the type or amount of therapeutic agent may be adjusted accordingly during the duration of the treatment, e.g., a succession of different hormonal agents and/or different agent concentrations may be employed to coincide with the patient's menstrual cycle.

The release regions of the present invention form at least a portion of the implantable or insertable medical devices of the present invention, and in some instances form the entire medical devices, in which case the materials forming the release region are selected to provide mechanical properties consistent with the intended function and operation of the implantable or insertable medical devices. A device may have a plurality of release regions. The base polymer can also be biodegradable to eliminate the need for removal.

Release regions for use in accordance with the devices of the present invention include carrier regions and barrier regions. By "carrier region" is meant a release region which further comprises a therapeutic agent and from which the therapeutic agent is released. Hence, in these embodiments, the release regions serve as a repository in which at least one therapeutic agent is present (e.g., dispersed and/or dissolved). For example, in some embodiments, a carrier region is disposed over all or a portion of a medical device substrate. In other embodiments, a carrier region constitutes the entirety of the medical device. In other embodiments, the medical device will comprise two or more distinct carrier regions, which may exist, e.g., as coaxial layers or as distinct sections lengthwise along the longitudinal axis of the device (e.g., a stent having distinct end regions of different durometer value and/or different therapeutic agent content with a transitional coextruded region in between).

By "barrier region" is meant a region which is disposed between a source of therapeutic agent and a site of intended release, and which controls the rate at which therapeutic agent is released. For example, in some embodiments, the medical device is provided with a barrier region that surrounds a source of therapeutic agent. In other embodiments, a barrier region is disposed over a source of therapeutic agent, which is in turn disposed over all or a portion of a medical device substrate.

Hence, in certain embodiments, release regions for use in accordance with the present invention are in the form of a release layers, which cover all or a part of a medical device substrate. As used herein a "layer" of a given material is a region of that material whose thickness is small compared to both its length and width. As used herein a layer need not be planar or conformal (for example, taking on the contours of an underlying substrate). Layers can be discontinuous (e.g., patterned). Terms such as "film," "layer" and "coating" may be used interchangeably herein.

As noted above, the release regions of the present invention comprise one or more polymers, typically at least 50 wt % polymers, at least 75 wt % polymers, at least 90 wt % polymers, at least 95 wt % polymers, or even more. The release regions may also contain therapeutic agents and further optional components, including but not limited to, radio-opacifying agents, colorants, and the like.

Numerous techniques are available for forming the polymeric release regions of the present invention. For example, where one or more polymers forming the release regions have thermoplastic characteristics, a variety of standard thermoplastic processing techniques can be used to form the release region, including compression molding, injection molding, blow molding, spinning, vacuum forming and calendaring, as well as extrusion into sheets, fibers, rods, tubes and other cross-sectional profiles of various lengths. In certain preferred embodiments, the device is formed using injection molding techniques. Although a wide array of polymers can be selected for making the devices of the present invention by processes such as injection molding, certain preferred polymers include EVA, polyurethanes, silicone and polyethylene.

Using these and other techniques, entire devices or portions thereof can be made. For example, an entire stent or uterine device can be extruded using the above techniques. As another example, a coating can be provided by extruding a coating layer onto a pre-existing stent or uterine device. As yet another example, a coating can be co-extruded along with an underlying stent body or uterine device body.

If the therapeutic agent is stable at processing temperatures, then it can be combined with the polymer(s) forming the release region prior to thermoplastic processing, producing a therapeutic-agent containing carrier region. If not, then a carrier region can nonetheless be formed by subsequent introduction of therapeutic agent, for example, as discussed below. For example, therapeutic agents can be imbibed into an already formed polymer such as a polymer pigtail tip of a ureteral stent.

In some embodiments, processing may comprise dry blending, compounding or otherwise mixing one or more polymers, one or more therapeutic agents, and any further optional agents to form a relatively homogeneous mixture thereof and then shaping the homogenous mixture into a carrier region of a medical device. The mixing and shaping operations, as described more fully below, may be performed using any of the conventional devices known in the art for such purposes.

In the following description, the one or more therapeutic agents and further optional agents will, at times, be collectively referred to as "additives" or "agents."

Mixing or compounding polymer(s) with one or more of the therapeutic agents and further optional agents to form a relatively homogeneous mixture thereof may be performed with any device known in the art and conventionally used for mixing polymeric materials with additives. Where thermoplastic materials are employed, a polymer melt is formed by heating the various agents, which can then be mixed to form a more homogenous mixture. A common way of doing so is to apply mechanical shear to a mixture of the polymer and additives. Devices in which the polymer and additives may be mixed in this fashion include, but are not limited to, devices such as a single screw extruder, a twin screw extruder, a banbury mixer, a high-speed mixer, and a ross kettle.

Mixing may also be achieved by dissolving polymer(s) of interest with one or more of the therapeutic agents and further optional agents in a solvent system, as described below.

Any of the polymer(s) and/or additives may be precompounded or individually premixed to facilitate subsequent processing.

The mixture of polymer and additives can be shaped into at least a portion of a medical device in accordance with the present invention by means of any process conventionally used to shape polymeric materials such as thermoplastic and elastomeric materials. Among such shaping processes are included, but not limited to, extrusion including coextrusion, molding, calendaring, casting and coating.

Coextrusion is a shaping process that is useful wherein at least a portion of a medical device in accordance with the present invention is a multilayer structure, for example, comprising one or more distinct carrier layers and one or more barrier layers at least partially covering a surface of a carrier layer. Multi-layer structures can also be formed by other processing and shaping techniques such as laminar injection molding (LIM) technology.

Alternatively, co-extrusion may comprise two polymer melts of different content, with or without additives, wherein, for example, the polymer melts are extruded according to a gradient such that the resultant medical device has sections with differing content. For example, melts producing polymeric regions of different durometer value may be extruded according to a gradient to form a device, such as a stent, with opposing end regions having respective polymer contents, and a transition region in between, which is a co-extrusion going from 100% of one polymer content at one end of the transition region to 100% of the other polymer content at the other end of the transition region. Other lengthwise co-extrusions are contemplated to form sections along the length of a medical device that have different polymer content, different therapeutic agents and/or different therapeutic agent concentrations.

Polymeric release regions can also be formed using solvent-based techniques in which one or more polymers are first dissolved or dispersed in a solvent and the resulting mixture is subsequently used to form a polymeric release region.

Where solvent-based techniques are used, the solvent system that is selected will contain one or more solvent species. The solvent system preferably is a good solvent for the polymer(s) within the release region and, where included, for the therapeutic agent and any supplemental additives. The particular solvent species that make up the solvent system may also be selected based on other characteristics including drying rate and surface tension.

Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In many embodiments, a mixture containing solvent, one or more polymers and where included, therapeutic agent and any supplemental additive, is applied to a substrate to form a release region. For example, the substrate can be all or a portion of an implantable or insertable medical device, such as a stent or a uterine device, to which a release layer is applied. On the other hand, the substrate can also be, for example, a template such as a mold from which the release region is removed after solvent elimination. Such template-based techniques are particularly appropriate for forming objects such as sheets, tubes, cylinders and so forth, which can be easily removed from a template substrate.

In other techniques, for example, fiber forming techniques, the polymeric release region is formed without the aid of a substrate or template.

Where appropriate, techniques such as those listed above can be repeated or combined to build up a release region to a desired thickness. The thickness of the release region can be varied in other ways as well. For example, in one preferred process, solvent spraying, coating thickness can be increased by modification of coating process parameters, including increasing spray flow rate, slowing the movement between the substrate to be coated and the spray nozzle, providing repeated passes and so forth.

Where a carrier region is formed (as opposed to, for example, a barrier region), a therapeutic agent can be provided in a polymer solution or melt, and hence co-established with the carrier region. In other embodiments, on the other hand, the therapeutic agent can be dissolved or dispersed within a solvent, and the resulting solution contacted with a previously formed polymer region using, for example, one or more of the application techniques described above (e.g., dipping, spraying, etc.).

Barrier layers, on the other hand, may be formed over a therapeutic-agent-containing region, for example, using thermoplastic or solvent-based techniques such as those discussed above. The barrier layer serves, for example, as a boundary layer to retard diffusion of the therapeutic agent, for example, acting to prevent a burst phenomenon whereby much of the therapeutic agent is released immediately upon exposure of the device or a portion of the device to the implant or insertion site.

In some embodiments, the therapeutic-agent-containing region beneath the barrier region will comprise one or more polymers such as those described elsewhere herein. The polymeric composition of the barrier region may, or may not, be the same as the polymeric composition of the underlying therapeutic-agent-containing region. As such, the therapeutic-agent-containing region can also be established using thermoplastic and solvent-based techniques such as those discussed above. In other embodiments, the therapeutic-agent-containing region beneath the barrier layer is established without an associated polymer. In this case, the therapeutic agent can simply be dissolved or dispersed in a solvent or liquid, and the resulting solution/dispersion can be contacted with a substrate again using, for instance, one or more of the above-described application techniques.

Where the release region is formed using a solvent-based technique, it is preferably dried after application to remove the solvents. The release region typically further conforms to any underlying surface during the drying process.

As indicated above, the polymers used in the urological and uterine devices of the present invention may be any biocompatible polymer suitable for use in implantable or insertable medical devices. The polymer may be substantially non-biodegradable or biodegradable.

Preferred substantially non-biodegradable biocompatible polymers include thermoplastic and elastomeric polymeric materials. Polymers for use in the devices of the present invention can be selected, for example, from polyolefins such as metallocene catalyzed polyethylenes, polypropylenes, and polybutylenes and copolymers thereof; vinyl aromatic polymers such as polystyrene; vinyl aromatic copolymers such as styrene-isobutylene copolymers and butadiene-styrene copolymers; ethylenic copolymers such as ethylene vinyl acetate (EVA), ethylene-methacrylic acid and ethylene-acrylic acid copolymers where some of the acid groups have been neutralized with either zinc or sodium ions (commonly known as ionomers); polyacetals; chloropolymers such as polyvinylchloride (PVC); fluoropolymers such as polytetrafluoroethylene (PTFE); polyesters such as polyethyleneterephthalate (PET); polyester-ethers; polyamides such as nylon 6 and nylon 6,6; polyamide ethers; polyethers; elastomers such as elastomeric polyurethanes and polyurethane copolymers; silicones; polycarbonates; and mixtures and block or random copolymers of any of the foregoing are non-limiting examples of non-biodegradable biocompatible polymers useful for manufacturing the medical devices of the present invention.

Among preferred non-biodegradable polymeric materials are polyolefins, ethylenic copolymers including ethylene vinyl acetate copolymers (EVA) and copolymers of ethylene with acrylic acid or methacrylic acid; elastomeric polyurethanes and polyurethane copolymers; metallocene catalyzed polyethylene (mPE), mPE copolymers, ionomers, and mixtures and copolymers thereof; and vinyl aromatic polymers and copolymers. Among preferred vinyl aromatic copolymers are included copolymers of polyisobutylene with polystyrene or polymethylstyrene, even more preferably polystyrene-polyisobutylene-polystyrene triblock copolymers. These polymers are described, for example, in U.S. Pat. No. 5,741,331, U.S. Pat. No. 4,946,899 and U.S. Pat. No. 6,545,097, each of which is hereby incorporated by reference in its entirety. Ethylene vinyl acetate (EVA) having a vinyl acetate content of from about 19% to about 28% is an especially preferred non-biodegradable material. EVA copolymers having a lower vinyl acetate content of from about 3% to about 15% are also useful in particular embodiments of the present invention as are EVA copolymers having a vinyl acetate content as high as about 40%. These relatively higher vinyl acetate content copolymers may be beneficial in offsetting stiffness from coextruded barrier layers. Among preferred elastomeric polyurethanes are block and random copolymers that are polyether based, polyester based, polycarbonate based, aliphatic based, aromatic based and mixtures thereof. Commercially available polyurethane copolymers include, but are not limited to, Carbothane®, Tecoflex®, Tecothane®, Tecophilic®, Tecoplast®, Pellethane®, Chronothane® and Chronoflex®. Other preferred elastomers include polyester-ethers, polyamide-ethers and silicone.

Preferred biodegradable polymers can be selected, for example, from polylactic acid, polyglycolic acid and copolymers and mixtures thereof such as poly(L-lactide) (PLLA), poly(D,L-lactide) (PLA); polyglycolic acid [polyglycolide (PGA)], poly(L-lactide-co-D,L-lactide) (PLLA/PLA), poly (L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL), poly(glycolide-co-caprolactone) (PGA/PCL); polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(phosphate ester), poly(amino acid) and poly(hydroxy butyrate), polydepsipeptides, maleic anhydride copolymers, polyphosphazenes, polyiminocarbonates, poly[(97.5% dimethyl-trimethylene carbonate)-co-(2.5% trimethylene carbonate)], cyanoacrylate, polyethylene oxide, polyvinyl alcohol (PVA), polyvinylpyrrolidone (PVP), chemically modified celluloses such as hydroxypropylmethylcellulose and regenerate cellulose, polysaccharides such as hyaluronic acid, chitosan, alginates and modified starch such as pentastarch and hydroxyethyl starch, proteins such as gelatin and collagen, and mixtures and copolymers thereof, among others.

The medical devices of the present invention, for example, the urological devices, may also contain a radio-opacifying agent within its structure. For example, the radio-opacifying agent may be present in or on any of the carrier or barrier regions found in the devices. The radio-opacifying agent facilitates viewing of the medical device during insertion of the device and at any point while the device is implanted. A radio-opacifying agent typically functions by scattering x-rays. The areas of the medical device that scatter the x-rays are detectable on a radiograph. Among radio-opacifying agents useful in the medical device of the present invention are included, but not limited to, bismuth subcarbonate, bismuth oxychloride, bismuth trioxide, barium sulfate, tungsten and mixtures thereof. Where present, the radio-opacifying agent is preferably present in an amount of from about 0.5% to about 90%, more preferably from about 10% to about 90% by weight, of the polymer. A particularly preferred amount of radio-opacifying agent is from about 10 to about 40% by weight of the polymer.

Other optional agents may include, for example, antimicrobial agents that have been added in an amount effective to inhibit the growth of microbes on or around the device as well as any antimicrobial agents added for therapeutic purposes. Antimicrobial agents include, for example, triclosan, chlorhexidine and combinations thereof. In some embodiments, a lubricious hydrophilic coating may be applied to the surface of the urological devices and uterine devices of the present invention.

A. Urological Devices

As used herein, the term "urological devices" include medical devices that are adapted for placement in any part of the human urinary tract, including ureteral and urethral stents, urinary catheters such as Foley catheters, and the like.

As discussed above, in one aspect of the invention, a urological medical device is provided comprising a first therapeutic agent for treating a urological condition, wherein the medical device is adapted, upon implantation or insertion into a patient, to release all or a majority of the first therapeutic agent from a portion of the medical device that occupies the urinary bladder.

Ureteral stents, for example, are typically used to facilitate urinary drainage from the kidney to the bladder in patients having a ureteral obstruction or injury, or to protect the integrity of the ureter in a variety of surgical manipulations. They are used, for example, in post endo-urological procedures to act as a scaffold in the event of ureteral obstruction secondary to the procedure. Stents are also used as palliative devices to provide patency in the presence of congenital defects, strictures or malignancies that cause a ureter obstruction.

Any of a number of ureteral stent designs may be employed for the present invention. For example, the urological device of the present invention may comprise a tubular member, a renal retention structure on the distal end of the tubular member and a bladder retention structure on the proximal end of the tubular member.

In some preferred embodiments, the ureteral stents of the present invention are formed based on the design of the Percuflex® Ureteral Stent, which is commercially available from Boston Scientific, Natick, Mass., USA. As would be appreciated by one of ordinary skill in the art, other ureteral stent designs may be employed such as that of the Contour™ Stent, also commercially available from Boston Scientific, and those disclosed in U.S. Pat. Nos. 6,656,146, 6,719,804, 6,685,744, and 6,648,863, all of which are commonly assigned to SciMed Life Systems, Inc., and the contents of which are incorporated by reference in their entirety.

Figure 1:
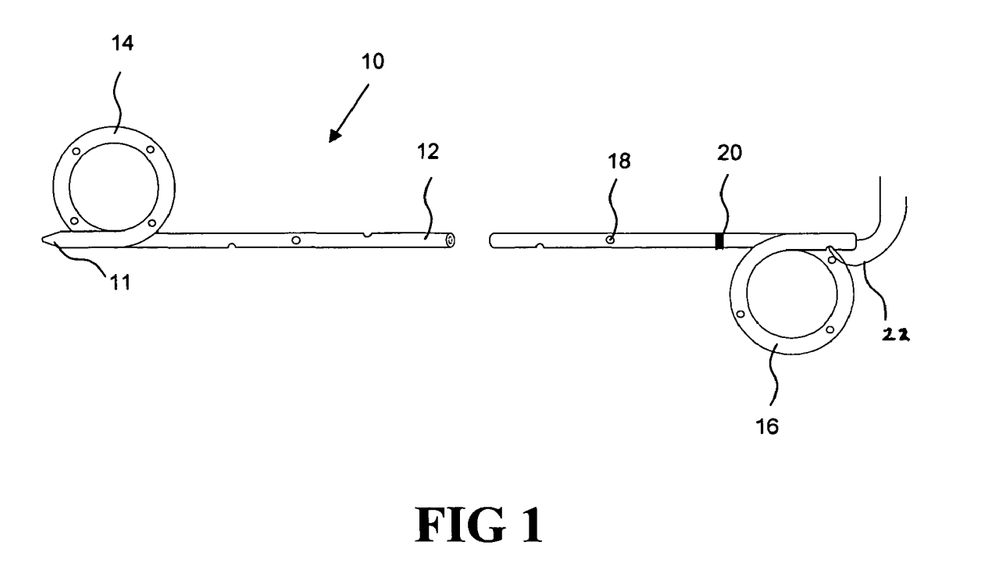
FIG. 1 is a simplified schematic representation of a urological device, specifically a ureteral stent, according to one embodiment of the present invention.

A schematic diagram of one exemplary stent 10 is illustrated in FIG. 1. Conventional retention structures typically include spirals, pigtails, coils, corkscrews, mallincotts, barbs, mushrooms or hook ends designed to retain the stent within the ureter and all are within the scope of the present invention. In some embodiments, the stent 10 is a tubular polymer extrusion containing a tubular member (e.g., shaft 12), a distal renal retention structure (e.g., renal pigtail 14), and a proximal retention structure (e.g., bladder pigtail 16). These retention structures prevent upward migration of the stent toward the kidney or downward migration of the stent into the ureter. In other embodiments, the proximal retention structure comprises a mallincott instead of a bladder pigtail. The tubular member may comprise a melt-extruded polymeric tubular shaft as well as those produced according to any number of other processing methods as detailed above.

Figure 2:
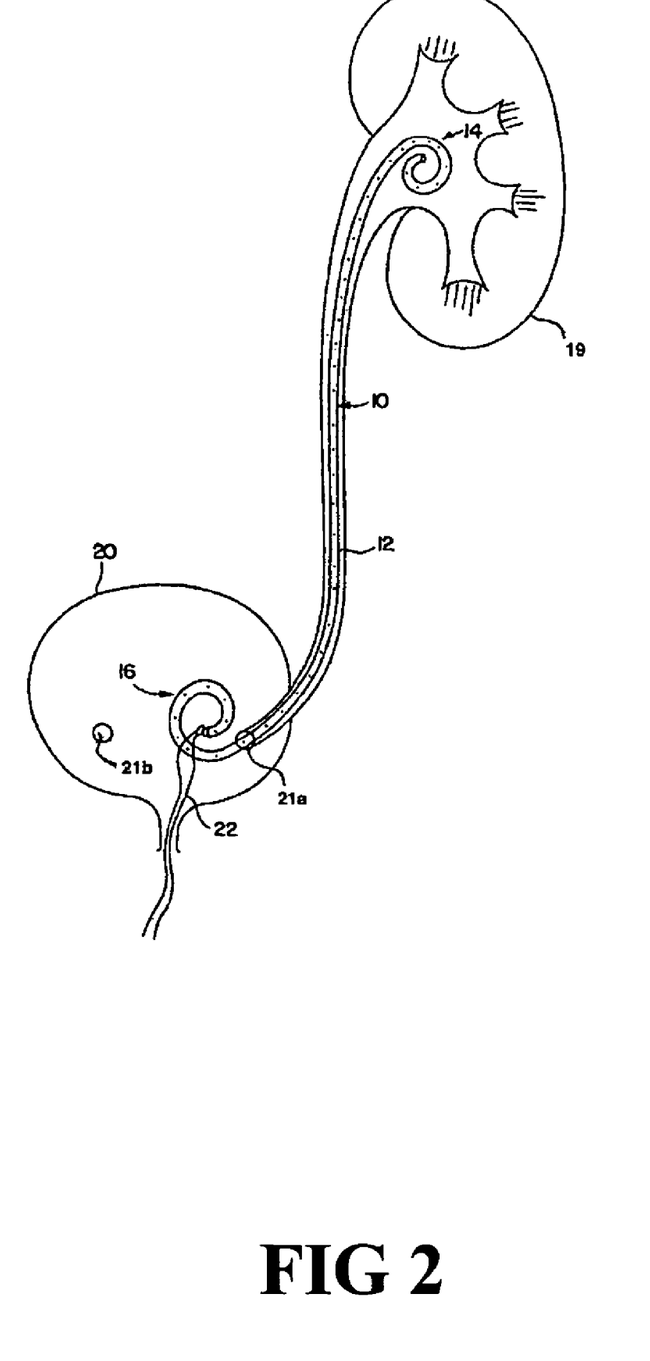
FIG. 2 shows the ureteral stent of FIG. 1 as positioned within the body using a standard catheter means. The stent is placed within the human urinary tract, which includes the renal pelvis, the kidney, the ureter, the urethra and the ureteral orifices opening into the bladder.

The stent 10 having two pigtails 14, 16, is inserted into the ureter to provide ureteral rigidity and to allow the passage of urine. The pigtails 14, 16 serve to keep the stent 10 in place once positioned by the physician. The stent 10, as exemplified by FIG. 1, may further be provided with any one or more of the following: (a) a tapered tip 11 (not shown), to aid insertion, (b) multiple side ports 18 (one numbered), which are typically arranged in a spiral pattern down the length of the body to promote drainage, (c) graduation marks 20 (one illustrated), which are normally used for visualization by the physician to know when the appropriate length of stent has been inserted into the ureter, and (d) a Nylon suture 22, which aids in positioning and withdrawal of the stent, as is known in that art. During placement, such ureteral stents 10 are typically placed over a urology guide wire, through a cystoscope and advanced into position with a positioner. Once the proximal end of the stent is advanced into the kidney/renal calyx, the guide wire is removed, allowing the pigtails 14, 16 to form in the kidney 19 and bladder 20, as shown in FIG. 2. The renal pigtail 14 of the stent may be closed or tapered, depending on the method of insertion (e.g., the use of a guide wire). As shown in FIG. 2, the stent extends through the ureteral orifice 21a and into the bladder. For clarity, the ureter entering bladder 20 through orifice 21b is not shown.

The bladder retention structure comprises a first release region that comprises a biocompatible polymer and the first therapeutic agent is disposed beneath or within the release region. The device may further comprise at least one other release region, contained in the tubular member or renal retention structure or both, which comprises a biocompatible polymer and beneath or within which a second therapeutic agent is disposed, which may be the same as or different from the first therapeutic agent.

As would be appreciated by one of ordinary skill in the art, the first release region and other release regions may contain the same therapeutic agent in different concentrations such that a concentration gradient exists in the device. The first release region may contain a higher concentration of the therapeutic agent than other release regions. Alternatively, the first and second therapeutic agents are different. For example, the bladder pigtail 16 alone can contain a therapeutic agent for treating interstitial cystitis such as pentosan polysulfate, heparin, amitripyline, imipramine, hydroxyzine, dihydrochloride, hydroxyzine hydrochloride, hyoscyamine sulfate, hyosyamine, oxybutynin chloride, flavoxate, urised, phenazopyridine hydrochloride, DMSO, sodium oxychlorosene, lidocaine, hydrocortisone sodium succinate, sodium bicarbonate, capsaicin, hyaluronic acid silver nitrate or bacillus of Calmette and Guerin (BCG), or a combination of one or more of these agents.

Also, the bladder pigtail 16 may comprise a higher concentration of these or other therapeutic agents than concentrations in the renal pigtail 14 or the shaft 12.

The urological device may also reside completely in the urinary bladder, and take any of a number of forms, including a hollow three dimensional structure comprising a balloon, an annular ring, a disk, or a shaft, or other structure adapted for residence entirely within the bladder. To facilitate removal of the structure from the body, the device may further comprise a retraction means for removing the device from the bladder and out of the body. Typically, the retraction means is attached to a proximal portion of the structure and can comprise, for example, a suture or thread.

In other embodiments, the urological device comprises a urinary catheter such as a Foley catheter having a balloon structure and a catheter tip wherein the polymer release region containing the therapeutic agent is disposed over all or a portion of the medical device substrate. For example, the polymer used to create the Foley catheter tip or balloon is mixed or compounded with a therapeutic agent such as heparin as described in the processing details above.

In yet other embodiments, the urological device of the present invention comprises a urethral stent wherein the carrier region containing the therapeutic agent is disposed at least over a portion of the stent that will be placed in or near the bladder.

Techniques for forming urinary stents, including urethral and ureteral stents, are described in detail in U.S. Patent Application Publication No. 2003/0153983 to Kathleen M. Miller et al., the disclosure of which is hereby incorporated by reference. In brief, methods are described for forming stents which contain (a) a therapeutic agent (b) a radio-opacifying agent, (c) a colorant and (d) the balance ethylene vinyl acetate (EVA) copolymer (e.g., Elvax 460, from DuPont). First, the therapeutic agent, radio-opacifying agent and colorant are pre-blended to produce a consistent, homogenous powder blend. The pre-blended mixture is then compounded with the EVA copolymer and extruded into pellets, which are then extruded into tubes of an appropriate diameter. For the stent devices, the extruded material is then cut, provided with a tapered tip, annealed, marked with ink and coated with a lubricious hydrophilic coating (Hydroplus™ (Union Carbide, Dow Chemical)), followed by side port formation, pigtail formation by hot air treatment, and the addition of the suture, as is known in the art.

In some other embodiments, only the pigtail portion of the device comprises a polymer release region containing or disposed over the therapeutic agents. Fabricated, for example, according to one of the processing techniques discussed above, in some embodiments, a preformed pigtail (e.g., a bladder pigtail containing a desired therapeutic agent) may be attached (e.g., thermally) to a stent main body to form a finished device. The stent main body itself may be comprised of any number of standard stent materials known in the art including polymeric or metallic materials.

"Therapeutic agents", "pharmaceutically active agents", "pharmaceutically active materials", "drugs" and other related terms may be used interchangeably herein and include genetic therapeutic agents, non-genetic therapeutic agents and cells. Therapeutic agents may be used singly or in combination. Therapeutic agents may be, for example, nonionic or they may be anionic and/or cationic in nature.

Exemplary therapeutic agents for use in connection with the urological devices of the present invention include: (a) non-steroidal anti-inflammatory agents (NSAIDS) (e.g., ibuprofen and naproxen); (b) steroidal anti-inflammatory agents (e.g., predisolone and dexamethasone; (c) antihistamines (e.g., hydroxyzine); (d) antidepressants such as tricyclic antidepressants (e.g., amitriptyline or imipramine) or a selective serotonin reuptake inhibitor (SSRI) such as fluoxetine, paroxetine or sertraline; (e) calcium channel blockers (e.g., nifedipine); (f) dimethyl sulfoxide (DMSO); (g) pentosan polysulfate sodium (PPS, Elmiron®); (h) anesthetic agents such as lidocaine, bupivacaine and ropivacaine; (i) heparinoid therapy including heparin; (j) heparin-binding epidermal growth factor-like growth factor (HB-EGF); (k) glycosaminoglycans (e.g., hyaluronic acid); (l) antibiotics such as Macrodantin® and Augmentin®; (m) analgesics such as salycylic acid; (n) antimicrobial agents such as triclosan, cephalosporins, aminoglycosides and nitrofurantoin; and (O) potassium chelating agents such as potassium citrate. Other therapeutic agents include sodium succinate, sodium bicarbonate, capsaicin, silver nitrate, or bacillus of Calmette and Guerin (BCG). Combinations of any of the foregoing are also used.

In preferred embodiments, the therapeutic agent comprises a combination of pentosan polysulfate and heparin.

Examples of non-steroidal anti-inflammatory drugs for use as therapeutic agents include: aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid, carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid and its derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ε-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts and esters thereof; as well as combinations thereof.

Examples of steroidal anti-inflammatory agents include prednisolone, methylprednisolone, hydrocortisone, flumethasone pivalate, triamcinolone, dexamethasone, betamethasone, amcinonide, and difluprednate.

B. Uterine Devices

The present invention is also directed to uterine devices for the treatment of uterine conditions which is adapted to conform to the general contours of an interior cavity of a human female uterus. The devices comprise at least one release region that controls the release of at least one therapeutic agent (which is disposed beneath or within the release region) for treating a uterine condition.

For example, in some embodiments, the uterine device comprises a contoured structure made of a flexible material having the general contours of an interior cavity of a mammalian (e.g., human) female uterus.

Figure 3A:
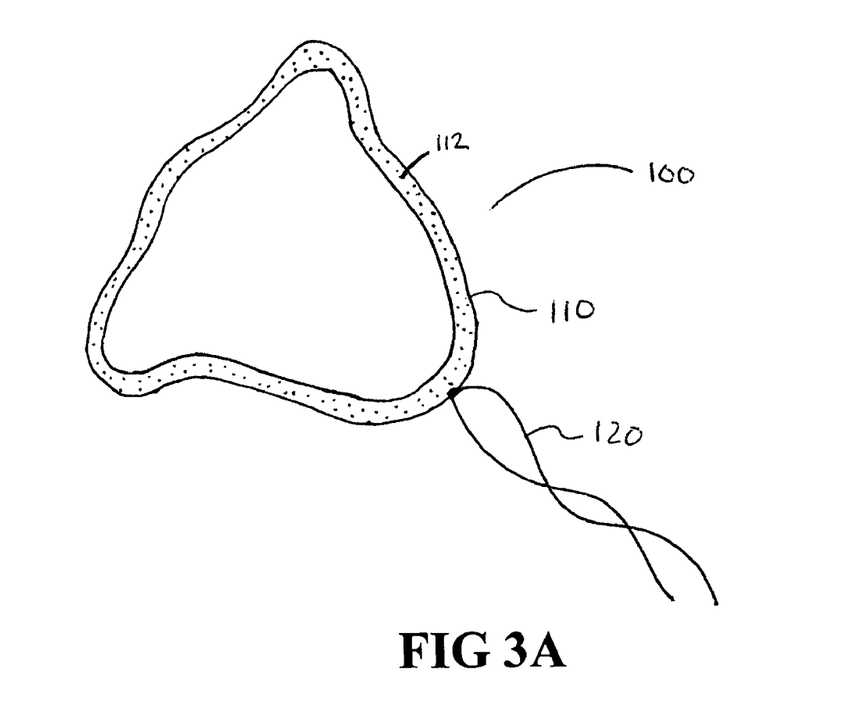
FIG. 3A is a schematic representation of a uterine device according to one embodiment of the present invention.

Referring to FIG. 3A, the present invention provides, in one embodiment, a uterine device 100 for the treatment of a uterine condition such as uterine fibroids. For instance, the device may comprise a contoured structure 110 made of a flexible material wherein an outer surface of the contoured structure 110 has the general contours of an interior cavity of a human female uterus. Thus, the contoured structure 110, may comprise a collapsible or inflatable three dimensional structure such as, for example, hollow three-dimensional structures like an inflatable "balloon," an irregular cone, irregular spheres, and the like. In addition to hollow three-dimensional structures, the contoured structure 110 may also comprise a continuous hoop of flexible material, e.g., irregular ring, and other predominantly two-dimensional structures whose length and width are appreciably greater than the thickness of the hoop. The contoured hoop, for example, may be made of a continuous length of a flexible material, e.g., a long cylinder, ribbon or tape of a soft polyurethane or other flexible polymeric material having a cross-sectional area that is circular, elliptical, rectangular, square, or the like. Both the hollow three-dimensional structures and the predominantly two-dimensional "hoops" are contoured such that when placed within the uterus, surface to surface contact between the outer surface of the device and the uterine wall is achieved. One or more therapeutic agents 112 are dispersed, dissolved or otherwise incorporated within a release region of the flexible material.

Figure 3B:
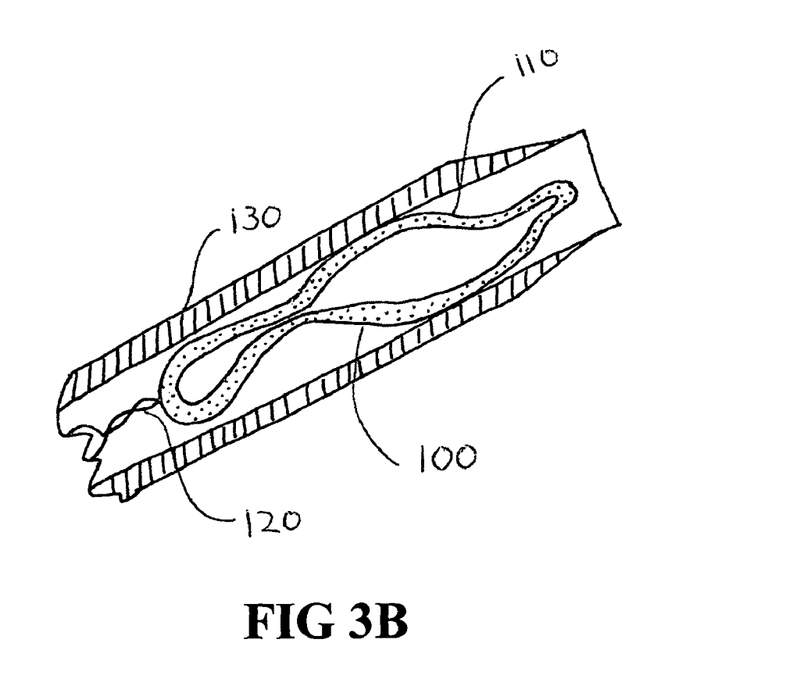
FIG. 3B is a cut-away schematic cross-sectional view of a device like that of FIG. 3A, withdrawn within a section of a delivery sheath.

To facilitate ease of insertion of the uterine device, the device may be compressed and withdrawn into a delivery sheath 130 as shown in FIG. 3B. Once the delivery sheath 130 has been placed through the cervix and into the uterine cavity, the sheath is retracted from the body. Due to the nature of the material forming the device, upon emerging from the sheath, the device self expands in the uterus to contact the walls of the uterus, described above, or is pushed into contact with the walls of the uterus, such as, for example, where the device is an inflatable balloon in the shape of the uterine cavity. Threads 120 or other means for removing the device from the body allow for easy extraction of the device upon completion of the treatment or replacement with a new uterine device 100 having other therapeutic agents 112 or the same therapeutic agent(s) at differing concentrations, for example, by pulling the device 100 into the sheath 130 to form a compressed configuration and then pulling the delivery sheath through the cervical opening and out of the body.

Figure 4:
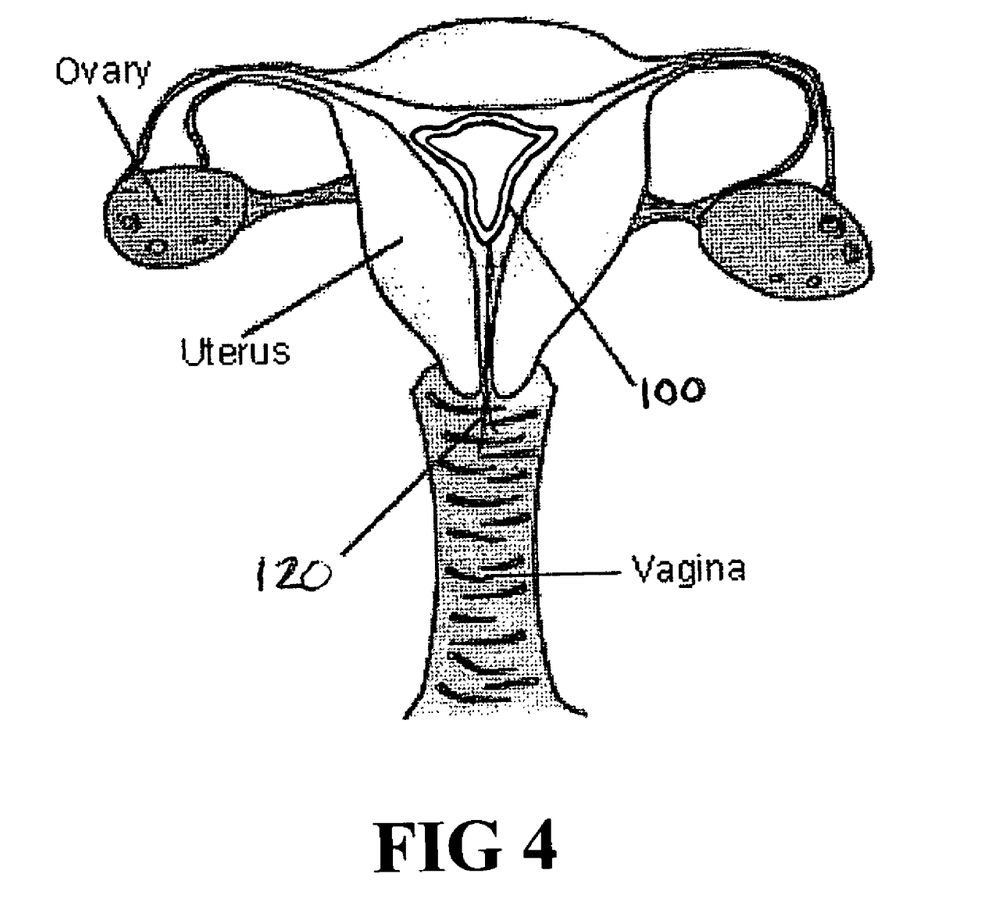
FIG. 4 is a simplified schematic representation of a uterine device like that of FIG. 3A, positioned within the uterus.

Referring to FIG. 4, a uterine device of the present invention as positioned within the uterus is shown. The size of the uterine device may be readily adapted to suit the size requirements of the individual patient. Generally, however, it is preferable that the general size of the device 100 be about the same or larger than that of the uterine cavity, such that upon deployment within the uterus, the device 100 exerts a positive tension in opposition to the uterine wall such that surface to surface contact between the device and the uterine wall is achieved. This facilitates direct contact and absorption of the therapeutic agents released by the device into the uterine lining where many conditions such as fibroids or endometriosis exist.

In alternative embodiments, the general shape of the uterine device may be that of typical intrauterine devices currently available as contraceptives (e.g., Mirena®, a T-shaped levonorgestrel-releasing intrauterine system sold by Berlex Laboratories) and other T-shaped intrauterine devices described, for example, in U.S. Pat. Nos. 3,993,057 and 4,578,076. In yet other embodiments, the device may be in the form of a concave disk that covers the cervix, similar in structure to diaphragms used for contraceptive purposes by women.

Exemplary therapeutic agents for use in connection with the uterine devices of the present invention include: (a) steroidal and non-steroidal anti-inflammatory agents (NSAIDS) such as dexamethasone, prednisolone, corticosterone, budesonide, estrogen, sulfasalazine and mesalamine; (b) contraceptives, (c) hormonal replacement therapy agents, and (d) GnRH agonists. Other therapeutic agents for the treatment of uterine conditions, in addition to the NSAIDs, contraceptives, and GnRH agonists discussed above include synthetic androgens, such as danazol (e.g., DANOCRINE®), antiprogestins, such as gestrinone and mifepristone (e.g., MIFEPREX®), selective progesterone receptor modulators (SPRMs), such as asoprisnil, selective estrogen receptor modulators (SERMs), and aromatase inhibitors, such as anastrozole (e.g., ARIMIDEX®), letrozole (e.g., FEMARA®) and exemestane (e.g., AROMASIN®), antiestrogens (e.g., tamoxifen and fulvestrant), among other agents.

Examples of non-steroidal and steroidal anti-inflammatory drugs for use as uterine treatment agents can be selected from those described above.

Examples of contraceptives for use as uterine fibroid treatment agents include: desogestrel, ethinyl estradiol, ethynodiol, ethynodiol diacetate, gestodene, lynestrenol, levonorgestrel, mestranol, medroxyprogesterone, norethindrone, norethynodrel, norgestimate, norgestrel, pharmaceutically acceptable salts and esters thereof, and combinations thereof. Specific examples include: norethynodrel/mestranol (e.g., ENOVID™), ethinyl estradiol/norethindrone (e.g., LOESTRIN™, BREVICON™, MODICON™, GENORA™, NELONA™, NORINYL™, OVACON-35™ and OVACON-50™), ethinyl estradiol/levonorgestrel (e.g., LEVLEN™, NORDETTE™, TRI-LEVLEN™ and TRIPHASIL-2™), ethinyl estradiol/norgestrel (e.g., LO/OVRAL™ and OVRAL™), ethinyl estradiol/ethynodiol diacetate (DEMULEN™), norethindrone/mestranol (e.g., NORINYL™, ORTHO-NOVUMO, NORETHIN™, GENORA™, and NELOVA™), ethinyl estradiol/desogestrel (e.g., DESOGEN™ and ORTHO-CEPT™), ethinyl estradiol/norgestimate (e.g., ORTHO-CYCLEN™ and ORTHO-TRICYCLEN™), norethindrone (e.g., MICRONOR™ and NOR-QD™), and norgestrel (e.g., OVRETTE™).

Examples of GnRH agonists for use as uterine fibroid treatment agents include: buserelin, cetorelix, decapeptyl, deslorelin, dioxalan derivatives, eulexin, ganirelix, gonadorelin hydrochloride, goserelin (ZOLADEX®), goserelin acetate, histrelin, histrelin acetate, leuprolide (e.g., LUPRON®), leuprolide acetate, leuprorelin, lutrelin, nafarelin (e.g., SYNAREL®) meterelin, triptorelin, further pharmaceutically acceptable salts and esters thereof, and combinations thereof.

Preferred therapeutic agents for the treatment of uterine conditions such as fibroids and endometriosis comprise, for example, LUPRON®, progestins, PANAZOL® and oral contraceptives.

Although various embodiments are specifically illustrated and described herein, it will be appreciated that modifications and variations of the present invention are covered by the above teachings and are within the purview of the appended claims without departing from the spirit and intended scope of the invention.

What is claimed is:

1. A urological medical device comprising a renal retention structure having a first release region and a bladder retention structure having a second release region, wherein the first and second release regions each comprise a biocompatible polymer and a first therapeutic agent disposed beneath or within the biocompatible polymer, wherein the first and second release regions both contain said first therapeutic agent in different concentrations such that a concentration gradient exists in the device, wherein the concentration of said first therapeutic agent is greater in the second release region than in the first release region.

2. The device of claim 1, wherein the urological condition comprises interstitial cystitis.

3. The device of claim 1, wherein said device further comprises a second therapeutic agent.

4. The device of claim 1, wherein said release region comprises a plurality of biocompatible polymers.

5. The device of claim 1, wherein said first therapeutic agent is released only from said second release region of the bladder retention structure.

6. The device of claim 1, wherein said device comprises a hollow three dimensional structure comprising a balloon, an annular ring, a disk, or a shaft.

7. The device of claim 1, wherein the device further comprises a retraction means for removing the device from the bladder and out of the body, wherein the retraction means is attached to a proximal portion of the structure.

8. The device of claim 7, wherein the retraction means comprises a suture or thread.

9. The device of claim 1, wherein at least one of the first and second release regions further comprises a second therapeutic agent, which is different from said first therapeutic agent.

10. The device of claim 1, wherein the first therapeutic agent comprises pentosan polysulfate or heparin, amitripyline, imipramine, hydroxyzine, dihydrochloride, hydroxyzine hydrochloride, hyoscyamine sulfate, hyosyamine, oxybutynin chloride, flavoxate, urised, phenazopyridine hydrochloride, DMSO, sodium oxychlorosene, lidocaine, hydrocortisone sodium succinate, sodium bicarbonate, capsaicin, hyaluronic acid silver nitrate or bacillus of Calmette and Guerin (BCG).

11. The device of claim 1, wherein the first therapeutic agent is released at higher concentrations in the bladder retention structure.

12. The device of claim 1, wherein the urological condition comprises interstitial cystitis.

13. The device of claim 1, wherein said release region(s) comprises a biocompatible biodegradable polymer.

14. The device of claim 13, wherein said biodegradable polymer is selected from the group consisting of polylactic acid, polyglycolic acid, polycaprolactone, and copolymers and mixtures thereof.

15. The device of claim 1, wherein said release region(s) comprise a biocompatible non-biodegradable polymer.

16. The device of claim 15, wherein said non-biodegradable polymer is selected from the group consisting of ethylene vinyl acetate copolymers, copolymers of ethylene with acrylic acid or methacrylic acid, elastomeric polyurethanes and polyurethane copolymers, metallocene catalyzed polyethylene, ionomers and vinyl aromatic copolymers.

17. The device of claim 15, wherein said non-biodegradable polymer is an ethylene vinyl acetate copolymer.

18. The device of claim 1, wherein the therapeutic agent is selected from the group consisting of non-steroidal anti-inflammatory agents, steroidal anti-inflammatory agents, antihistamines, tricyclic antidepressants, selective serotonin reuptake inhibitors, calcium channel blockers, dimethyl sulfoxide, pentosan polysulfate sodium, anesthetic agents comprising lidocaine, bupivacaine and ropivacaine, heparinoids comprising heparin, heparin-binding epidermal growth factor-like growth factor, glycosaminoglycans comprising hyaluronic acid, antibiotics, analgesics comprising salicylic acid, antimicrobial agents comprising triclosan, cephalosporins, aminoglycosides or nitrofurantoin, potassium chelating agents comprising potassium citrate, sodium succinate, sodium bicarbonate, capsaicin, silver nitrate, and bacillus of Calmette and Guerin, or combinations thereof.

19. The device of claim 1, wherein the therapeutic agent is selected from the group consisting of pentosan polysulfate sodium and heparin, or combinations thereof.

20. The device of claim 1, wherein said polymer further comprises a radio-opacifying agent.

21. The device of claim 1, wherein said release region is a barrier layer at least partially covering a source of therapeutic agent.

22. The device of claim 1, further comprising an antimicrobial agent present in an amount effective to inhibit the growth of microbes on and around the device.

23. The device of claim 1, wherein the antimicrobial agent is selected from the group consisting of triclosan, chlorhexidine and combinations thereof.

24. The device of claim 1, further comprising a lubricious hydrophilic coating on a surface of said device.

25. The device of claim 1, wherein said device comprises a melt-extruded polymeric tubular shaft.

26. The device of claim 1, wherein the device comprises a ureteral stent, a urethral stent or a urinary catheter.

* * * * *